United States Patent [19]

Insall et al.

[11] Patent Number: 5,108,401

[45] Date of Patent: Apr. 28, 1992

[54] PATELLA CUTTING CLAMP

[75] Inventors: John N. Insall; Steven B. Haas, both of New York, N.Y.; James M. Carr, Cos Cob, Conn.

[73] Assignee: New York Society for the Relief of the Ruptured and Crippled, Maintaining the Hospital for Special Surgery, New York, N.Y.

[21] Appl. No.: 685,452

[22] Filed: Apr. 12, 1991

[51] Int. Cl.$^5$ .............................................. A61F 2/38
[52] U.S. Cl. ....................................... 606/79; 606/82; 606/87
[58] Field of Search ................. 606/79, 82, 83, 53, 606/86, 87, 88, 89, 96, 104

[56] References Cited

U.S. PATENT DOCUMENTS

| | | | |
|---|---|---|---|
| 1,676,574 | 7/1928 | Ostermeier | 606/83 |
| 2,566,626 | 9/1951 | Otto | 606/83 |
| 4,462,403 | 7/1984 | Martin | 606/83 |
| 4,633,862 | 1/1987 | Petersen | 606/82 X |
| 4,722,338 | 2/1988 | Wright et al. | 606/83 |
| 4,777,948 | 10/1988 | Wright | 606/83 |
| 5,019,081 | 5/1991 | Watanabe | 606/79 |

FOREIGN PATENT DOCUMENTS 230503  1/1911  Fed. Rep. of Germany ........ 606/83

*Primary Examiner*—Robert A. Hafer
*Assistant Examiner*—Sam Rimell
*Attorney, Agent, or Firm*—Brumbaugh, Graves, Donohue & Raymond

[57] ABSTRACT

A patella cutting clamp comprises a pair of jaw members joined together in scissors-like relation for pivotal movement relative to each other about a pivot axis intermediate their ends. Each jaw member has a handle portion extending in one direction from the pivot axis and a jaw portion extending in the other direction. The jaw portions have edges facing each other that are shaped for engagement with opposite borders of a patella. Teeth along the patella-gripping edges grip and hold the patella firmly. Saw guide slots in the jaw portions lying in a common plane guide the saw when the saw cut is made. A patella elevator member is attached to the jaw members for movement along the pivot axis and has a platform portion adapted to engage the anterior aspect of the patella. A mechanism is provided for establishing and maintaining a predetermined position of the elevator member relative to the jaw members and thereby positioning the patella at a predetermined position relative to the saw guide slots. Another mechanism holds the jaw members in an adjusted position relative to each other with the jaw portions engaging and holding the patella.

9 Claims, 3 Drawing Sheets

PATELLA CUTTING CLAMP

BACKGROUND OF THE INVENTION

The number of total knee joint replacement operations performed throughout the world is large and growing. In 1989 approximately 250,000 of such operations were performed worldwide, roughly half of them being performed in the United States. The majority of total knee replacements require resurfacing of the patella, which involves removing a several millimeters thick section of the bone and cartilage from the articular surface and replacing the removed section with a plastic implant, which is cemented to the vestigial patella. The section is usually removed by cutting it with a saw, one member of the surgical team holding the patella by hand and another member making a free hand saw cut.

The success of the resurfacing procedure requires that the patella be cut such that the vestigial patella is of the correct thickness and the sawn surface is flat, even and properly oriented. The most common complications after total knee replacement involve the patella. It is believed that many of those complications are a result of inconsistent and poorly aligned saw cuts of the patella. Thus far no instrument for aiding the surgeon in making the required saw cut of the patella has proven satisfactory.

SUMMARY OF THE INVENTION

The main object of the invention is to provide an instrument for holding the patella securely while the saw cut is made and for guiding the saw blade so that the saw cut is flat, even and accurately located. Another object is to facilitate locating the patella relative to the saw guide in the correct position for making the saw cut. A further object is to provide an instrument that can be used for a full range of sizes and shapes of patellas encountered in the operating room patient population. It is also desired that the interference of the instrument with the soft tissue surrounding the patella be minimized. Yet another object is that the instrument be easy to use and thoroughly reliable.

The foregoing objects are attained, according to the present invention, by a patella cutting clamp comprising a pair of jaw members joined together in scissors-like relation for pivotal movement relative to each other about a pivot axis intermediate their ends. Each jaw member has a handle portion extending in one direction from the pivot axis and a jaw portion extending in the other direction. The jaw portions have edges facing each other that are shaped for engagement with opposite borders of a patella, teeth along the patella-engaging edges adapted to grip and hold the patella firmly, and saw guide slots lying in a common plane. A patella elevator member is attached to the jaw members for movement along an axis substantially perpendicular to the plane of the saw guide slots and has a platform portion adapted to engage the anterior aspect of the patella. A mechanism is provided for establishing and maintaining a predetermined position of the elevator member relative to the jaw members and thereby holding the patella at a predetermined position relative to the saw guide slots. Another mechanism holds the jaw members in an adjusted position relative to each other with the jaw portions engaging and holding the patella.

In a preferred embodiment an elevator base is joined to the jaw members for pivotal movement about the pivot axis and receives the elevator member for movement solely along the pivot axis. Springs interposed between the respective jaw members and the elevator base maintain automatically the elevator member centered between the jaw portions throughout the range of adjustment of the jaw members. The elevator base includes a boss portion received through holes in the jaw members and joining them for pivotal movement. The elevator member further includes a mounting post portion received non-rotatably through the boss portion of the elevator base, and the post portion has a threaded portion that receives an elevator finger nut for adjusting the position of the elevator member along the pivot axis. A detent acting between the elevator base and the elevator finger nut holds the elevator finger nut in a selected one of a multiplicity of rotational positions against unwanted rotation caused by vibration induced by the saw. A scale on the elevator member indicates the position of the elevator member axially of the pivot axis relative to the jaw members, thereby enabling the surgeon to determine readily how thick the vestigial patella will be after the saw cut is made.

A preferred embodiment of the clamp also includes a mechanism for holding the jaw members in their adjusted position in engagement with the patella, such as a jaw-locking screw attached to the handle portion of one of the jaw members and passing through a hole in the other jaw member and a jaw-locking finger nut received on the screw and engaging said other jaw member. Advantageously, there is a detent associated with the jaw-locking finger nut and the jaw member that resiliently holds the finger nut in its adjusted position and prevents unwanted rotation of the finger nut caused by vibrations of the saw.

For a better understanding of the invention reference may be made to the following description of an exemplary embodiment, taken in conjunction with the accompanying drawings.

DESCRIPTION OF THE EMBODIMENT

Figure 1:
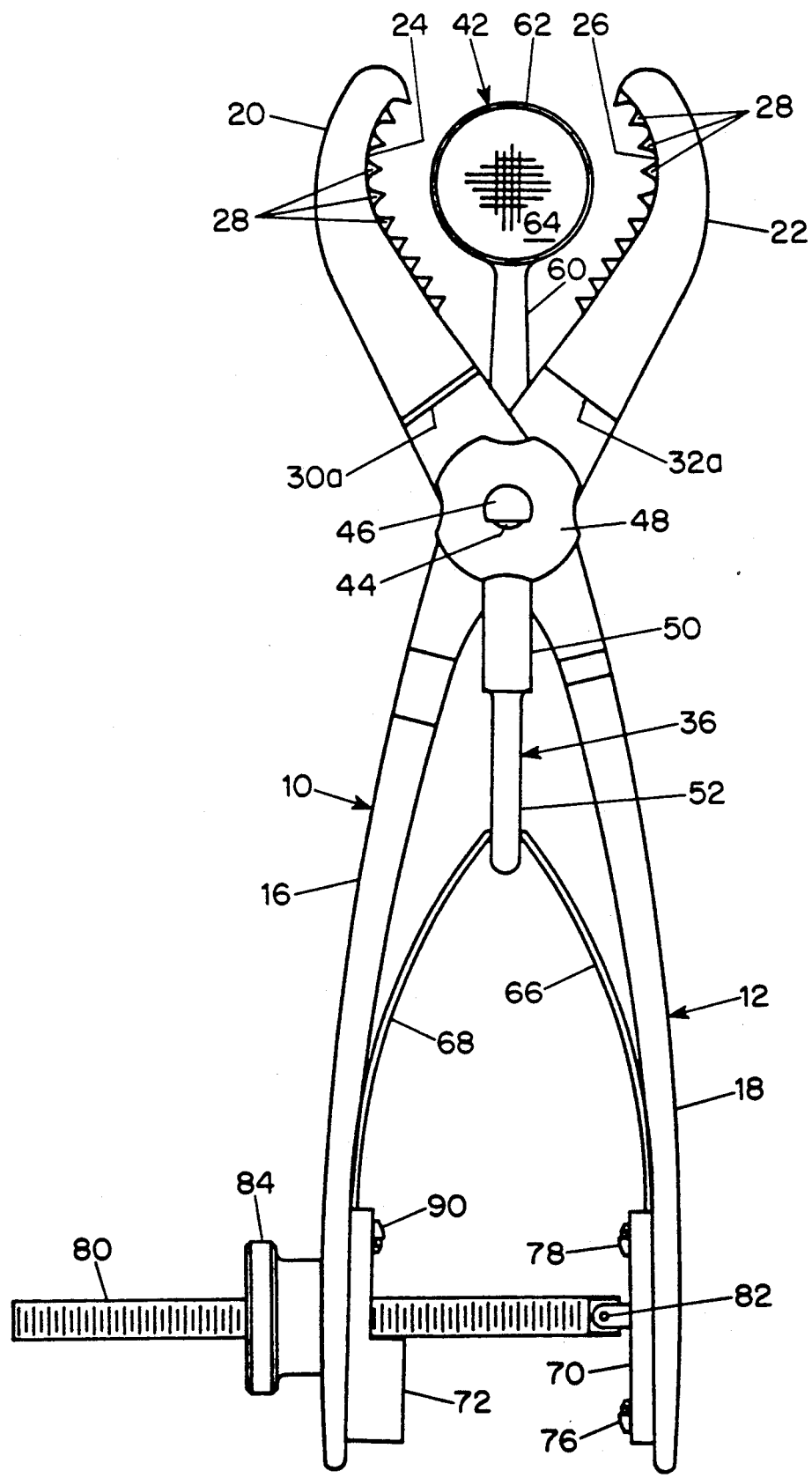
FIG. 1 is a top plan view of the embodiment in which all dashed lines representing hidden elements are omitted.

A pair of elongated jaw members 10 and 12 are joined together in a scissors-like manner for pivotal movement relative to each other about a pivot axis 14 intermediate their ends. Right and left handle portions 16 and 18 extend toward one end from the pivot axis, and right and left jaw portions 20 and 22 extend in the other direction. The top and bottom surfaces of the handle portions 16 and 18 are coplanar over most of their extents, are thicker than the jaw portions, and have offsets on both the top and bottom surfaces adjacent the pivot axis 14 where they overlap in regions that are reduced to one-half the total thickness of the jaw portions. The top and bottom surfaces of the jaw portions are coplanar over most of their extents, i.e., where they do not overlap. The external surfaces of the handle portions 16 and 18 of the jaw members are knurled (not shown) to provide a sure grip for the surgeon.

The edges 24 and 26 of the respective jaw portions that face each other are carefully shaped to engage the superior and inferior borders of the patella and have teeth 28 for gripping the patella securely by penetrating a small distance into it. The parts of the jaw portions 20 and 22 near the distal ends are of relatively greater curvature to accept and grip the narrower inferior aspects of all sizes of patellas, while the overall lengths and range of curvatures of the edges 24 and 26 are such that the broader superior borders of patellas of all sizes may be gripped by each jaw portion. The patella cutting clamp can be used for either a right of a left patella. It is not necessary for all of the teeth to penetrate the patella—it is sufficient for a few of the teeth on each jaw portion to do so.

Figure 2:
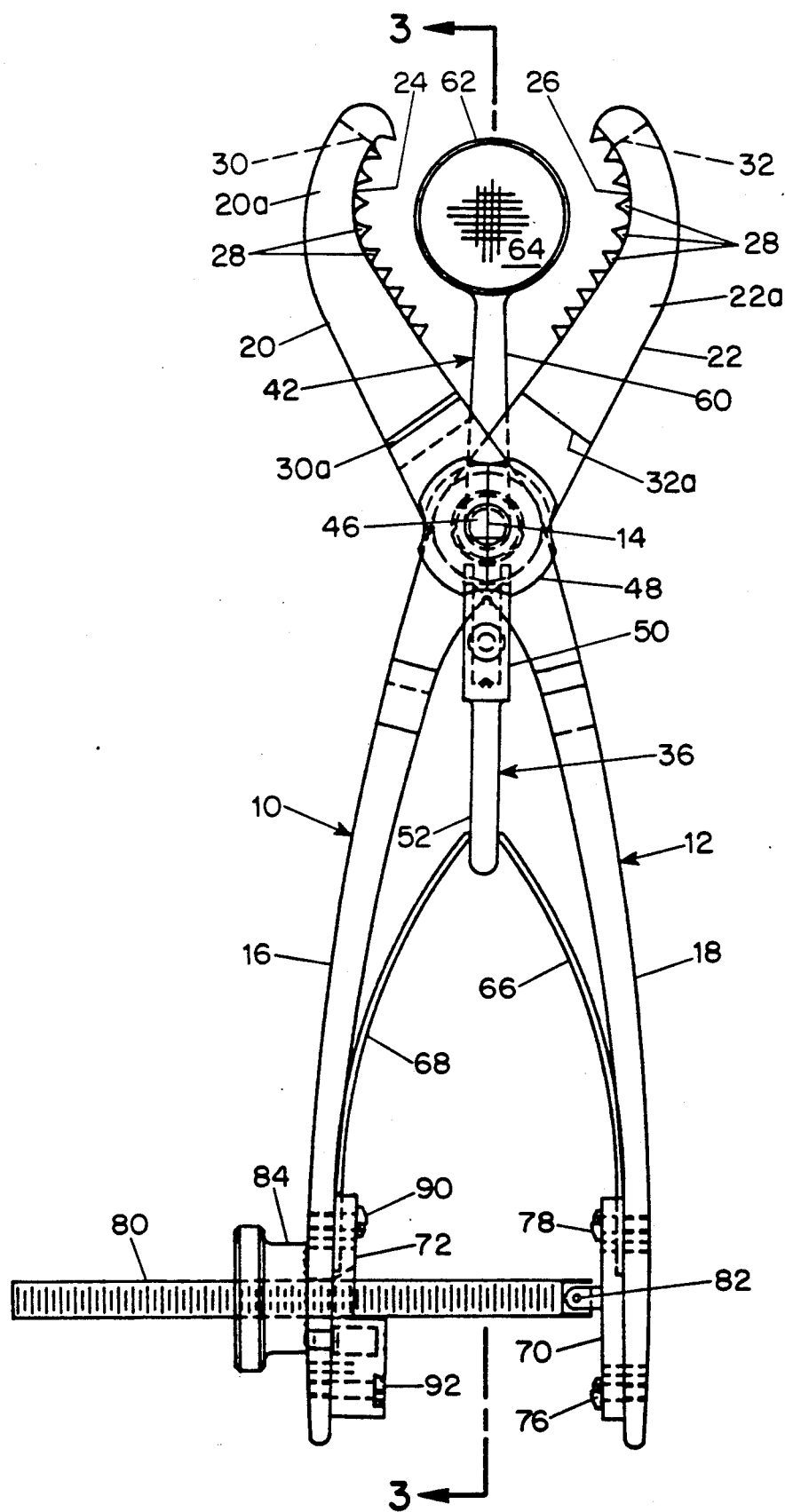
FIG. 2 is a top plan view in which dashed lines indicating hidden elements are included.

The jaw portions 20 and 22 have saw guide slots 30 and 32 that lie in a common plane. The slots in both jaw portions extend almost to the distal ends, as indicated by the dashed lines in FIG. 2 The slot 30 in the left jaw portion 20 is defined by a cantilevered portion 20a of the jaw portion 20 that extends from near the distal end in the proximal direction to a location near the pivot axis where it opens to the upper surface at a narrow transverse slit 30a. The slot in the right jaw portion 22 is defined by a cantilevered portion 22a that extends from near the distal end of the right jaw portion in the proximal direction to a proximal end 32a near the pivot axis.

The jaw members are joined together at the pivot axis 14 by a boss portion 34 of an elevator base member 36. The boss portion has a circular cylindrical peripheral surface that is received with a sliding fit through circular holes in the jaw members. The distal end of the boss portion is threaded and receives a nut 38 that holds the jaw members together, the nut bearing against a shoulder on the boss portion 34 so that the jaw members are not clamped to each other but are free to pivot about the pivot axis. A mounting post portion 40 of an elevator member 42 is received for axial sliding in a hole in the boss portion of the elevator base member but is prevented from rotating in the hole by a flat face 44. A threaded distal portion 46 of the elevator post portion receives an elevator-adjusting finger nut 48. An elevator locking ball housing 50 is affixed to an arm portion 52 of the elevator base member by locating pins 54 and a screw 56. A spring-loaded ball 58 in the housing 50 engages any one of several notches in the base wall of a peripheral groove 59 in the elevator finger nut. The ball housing 50 extends into the groove and holds it with a sliding fit in engagement with the elevator base member so that when the finger nut is rotated, it drives the elevator member axially along the pivot axis and changes the distance between the jaw members and the elevator member.

An arm portion 60 of the elevator member carries a cup portion 62. The concave surface 64 of the cup portion bears against the anterior surface of the patella and is knurled to enhance a frictional gripping of the patella Leaf springs 66 and 68 fastened to the handle portions of the jaw members by a jaw-locking screw mount 70 and a jaw-locking plunger housing 72 resiliently engage with a preload the arm portion 52 of the elevator base member and keep it centered between the handle portions, thereby also keeping the cup portion of the elevator member centered between the jaw portions of the jaw members in all positions of opening and closing of the jaw members. The leaf springs bias the jaw members toward an open position.

Figure 5:
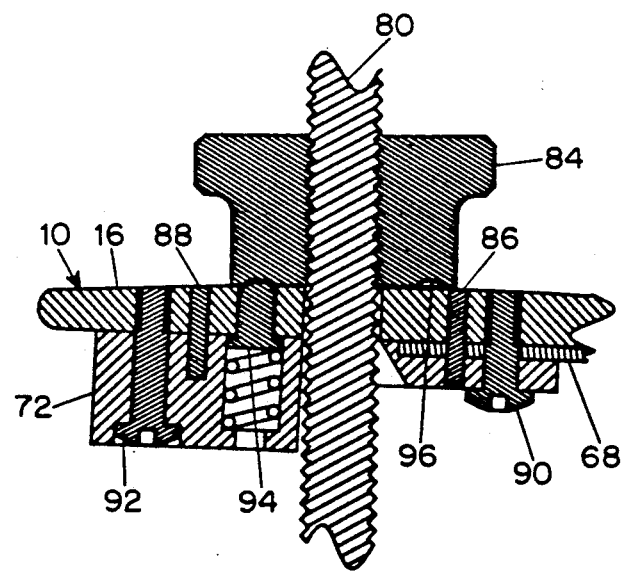
FIG. 5 is a fragmentary detail top cross-sectional view on a larger scale than FIG. 2 of the detent of the mechanism for holding the instrument in the clamped condition in engagement with the patella.

The jaw-locking screw mount 70 is fastened by screws 76 and 78 to the jaw member 18, and one end of a jaw-locking screw 80 is pivotally attached to it by an axle 82. The jaw-locking screw passes through a hole 81 in the other jaw member 16 As may best be seen in FIG. 5, a jaw-locking finger nut 84 is threaded onto the other end of the screw 80. The jaw-locking plunger housing 72 is fastened to the jaw member 16 by locating pins 86 and 88 and screws 90 and 92. A spring-loaded plunger 94 releasably engages any one of a series of notches 96 arranged in a circular row on the inner end face of the finger nut 84, thereby restraining the nut, as a detent, from rotating from any selected position in the absence of a predetermined force.

Figure 3:
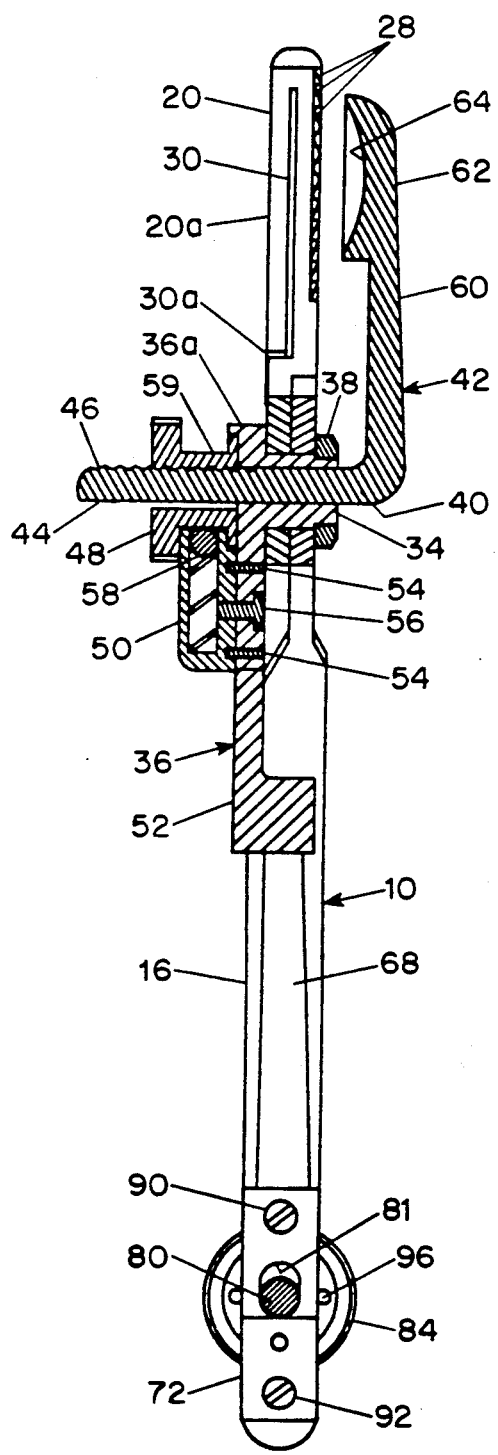
FIG. 3 is a side cross-sectional view taken along the lines 3—3 of FIG. 2.
Figure 4:
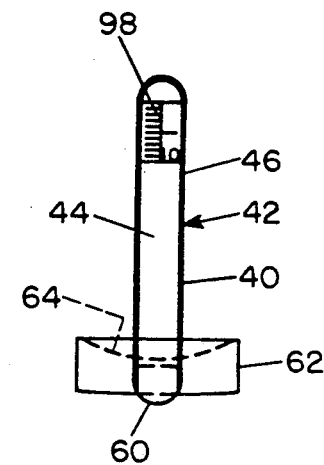
FIG. 4 is an end elevational view of the elevator member of the embodiment, as viewed from the handle end.

To accommodate a range of sizes and shapes of patellas, two elevator members, differing in cup size and shape, are provided. The appropriate elevator member 42 is inserted into the elevator base 36, and the finger nut 48 is threaded onto it. The desired spacing of the elevator cup portion 42 from the saw guide slots 30, 32 is established by rotating the finger nut. A scale 98 (FIG. 4) on the mounting post portion 40 of the elevator member 42 indicates the spacing. When an elevator member 50 is not in place in the instrument, the finger nut 48 is retained (kept from falling out) by the locking ball housing 50 and a lip or flange 36a (see FIG. 3) on the elevator base member that borders the base of the finger nut.

With the jaws opened, the instrument is positioned with the inverted patella centered between the jaws, its anterior surface lying in the cup portion 62 of the elevator member 42 and the bottoms of the jaws lying across the extensor mechanism of the knee joint. Because the patella and extensor mechanism are captured in the antero-posterior direction between the elevator cup portion and the jaw portions of the jaw members with the then-inverted anterior aspect of the patella engaging the cup portion from underneath and the jaw portions lying across the extensor mechanism from above, the extensor mechanism is stretched and forces the anterior aspect of the patella against the cup portion, thereby firmly holding the patella in engagement with the cup portion and ensuring the desired spacing between the anterior aspect of the patella and the saw guide slots. The patella is oriented correctly with the plane of the saw guide slots 30, 32, and the handle portions 16 and 18 of the jaw members are squeezed until the jaw portions 20, 22 grip the superior and inferior borders of the patella securely. As the jaw members are squeezed to grip the patella, the leaf springs 66, 68 keep the cup portion of the elevator member equidistant between the jaw portions. With the patella firmly gripped by the jaw members, the jaw-locking finger nut 84 is screwed down to bear against the handle portion 16. The saw blade is inserted into the saw guide slots 30, 32 and the saw cut is made. The detents associated with the elevator-locking finger nut and the jaw-locking finger nut secure them against unwanted rotation caused by vibration induced by the action of the saw blade. After the saw cut is made, the jaw-locking finger nut is backed off, and the jaws are opened to release the sawn patella.

We claim:

1. A patella cutting clamp comprising a pair of jaw members joined together in scissors-like relation for pivotal movement relative to each other about a pivot axis intermediate their ends, each jaw member having a handle portion extending in one direction from the pivot axis and a jaw portion extending in the other direction and the jaw portions having edges facing each other that are shaped for engagement with opposite borders of a patella, having teeth along said edges adapted to grip and hold the patella firmly, and having saw guide slots lying in a common plane; a patella elevator member attached to the jaw members for movement along the pivot axis and having a platform portion adapted to engage the anterior aspect of the patella; means for establishing and maintaining a predetermined position of the elevator member relative to the jaw members and thereby holding the patella at a predetermined position relative to the saw guide slots; and means for holding the jaw members in an adjusted position relative to each other with the jaw portions engaging and holding the patella.

2. A patella cutting clamp according to claim 1 and further comprising an elevator base joined to the jaw members for pivotal movement about the pivot axis and receiving the elevator member for movement solely along the pivot axis; and spring means interposed between the respective jaw members and the elevator base to maintain automatically the elevator member centered between the jaw portions throughout the range of pivotal adjustment of the jaw members.

3. A patella cutting clamp according to claim 2 wherein the elevator base includes a boss portion received through holes in the jaw members and joining them for pivotal movement.

4. A patella cutting clamp according to claim 3 wherein the elevator member further includes a mounting post portion received non-rotatably through the boss portion of the elevator base, and the shaft portion has a threaded portion that receives an elevator finger nut for adjusting the position of the elevator member along the pivot axis.

5. A patella cutting clamp according to claim 4 and further comprising detent means acting between the elevator base and the elevator finger nut for holding the elevator finger nut in a selected one of a multiplicity of rotational positions against unwanted rotation.

6. A patella cutting clamp according to claim 1 and further comprising a scale on the elevator member indicative of its position axially of the pivot axis relative to the saw guide slots.

7. A patella cutting clamp according to claim 1 and further comprising means for releasably holding the jaw members in their adjusted position in engagement with the patella.

8. A patella cutting clamp according to claim 7 wherein the means for holding the jaw members in their adjusted position includes a jaw-locking screw attached to the handle portion of one of the jaw members and passing through a hole in the other jaw member and a jaw-locking finger nut received on the screw and engaging said other jaw member.

9. A patella cutting clamp according to claim 8 wherein the jaw member holding means includes detent means associated with the jaw-locking finger nut and said other jaw member for preventing unwanted rotation of the jaw-locking finger nut.

* * * * *